United States Patent
Qualkinbush et al.

(10) Patent No.: US 6,378,224 B1
(45) Date of Patent: Apr. 30, 2002

(54) APPARATUS FOR REMOVING ODOR AND MOISTURE FROM FOOTWEAR AND THE LIKE

(76) Inventors: Carol M. Qualkinbush, 2421 Simpson St., Evanston, IL (US) 60201; Kitty D. Bendixen-park, 612 Michigan Ave., Evanston, IL (US) 60202

( * ) Notice: Subject to any disclaimer, the term of this patent is extended or adjusted under 35 U.S.C. 154(b) by 0 days.

(21) Appl. No.: 09/699,527

(22) Filed: Oct. 30, 2000

Related U.S. Application Data
(60) Provisional application No. 60/159,856, filed on Oct. 15, 1999.

(51) Int. Cl.⁷ ............................. F26B 19/00; B32B 5/16
(52) U.S. Cl. ......................... 34/80; 34/104; 428/307.7
(58) Field of Search ................... 34/103, 104, 105, 34/80, 89.1; 36/3 B, 30 A, 30 R, 44; 428/53, 307.7

(56) References Cited

U.S. PATENT DOCUMENTS

| | | | |
|---|---|---|---|
| 896,536 A | 8/1908 | Hayden | 12/114.2 |
| 2,173,528 A | 9/1939 | Beale | 12/128 |
| 3,131,036 A | 4/1964 | Hirschberg | 34/95 |
| D258,995 S | 4/1981 | Kuntzman | D2/315 |
| 4,497,080 A * | 2/1985 | Inspector | 12/128 |
| 5,109,805 A | 5/1992 | Baldry et al. | 119/173 |
| 5,261,169 A | 11/1993 | Williford | 36/43 |
| 5,291,669 A | 3/1994 | Khoury | 34/95 |
| 5,542,191 A * | 8/1996 | Shouse et al. | 34/104 |
| 5,732,485 A | 3/1998 | Laughlin | 36/136 |
| 5,733,826 A | 3/1998 | Groitzsch | 442/364 |
| 5,762,023 A | 6/1998 | Carter | 119/173 |
| 5,826,349 A | 10/1998 | Goss | 36/3 R |
| 5,826,543 A | 10/1998 | Raymond et al. | 119/173 |
| 5,829,167 A | 11/1998 | Valenzuela | 36/3 B |
| 5,918,379 A * | 7/1999 | Cooke | 34/105 |
| 5,921,003 A | 7/1999 | Kim | 36/3 B |
| 5,930,913 A | 8/1999 | Liao et al. | 34/104 |
| 5,950,323 A | 9/1999 | Wroth et al. | 34/104 |
| 5,951,799 A | 9/1999 | Williamson et al. | 156/148 |
| 6,006,447 A * | 12/1999 | Neal et al. | 36/3 |
| 6,032,295 A * | 3/2000 | Marshall | 2/239 |

OTHER PUBLICATIONS

Amethyst Galleries, Inc., *The Zeolite Group of Minerals*, website pages (1999/2000).
Imtek Environmental Corporation, *Consumer Odor Control Products Catalog*, website pages (1997/1998).
Combe Incorporated, *Foot Care*, website pages (1998).

* cited by examiner

*Primary Examiner*—Denise L. Esquivel
*Assistant Examiner*—Greg T. Warder
(74) *Attorney, Agent, or Firm*—Michael Best & Friedrich

(57) ABSTRACT

The present invention provides an odor and moisture removing apparatus and method of manufacturing the same which is suitable for insertion in a shoe or boot. The apparatus includes an outer shell which encloses layers of a woven porous fabric. A porous and absorbent felted material such as "silence cloth" is enclosed between the top/bottom layers and the layers holding the desiccant material. Further, a desiccant material is included between the second and third layers. As embodied, the apparatus is designed to resemble an animal-like creature for added novelty value and customer appeal. Further, an essential oil or fragrance such as vanilla or cinnamon is infused within a portion of the apparatus to mask or further eliminate any remaining odors in the footwear.

14 Claims, 6 Drawing Sheets

_US 6,378,224 B1_

APPARATUS FOR REMOVING ODOR AND MOISTURE FROM FOOTWEAR AND THE LIKE

This application claims benefit of Provisional No. 60/159,856 filed Oct. 15, 1999.

BACKGROUND OF THE INVENTION

1. Field of the Invention

This invention relates to an apparatus for removing odor and moisture and the like from substantially confined areas. More particularly, the invention relates to an apparatus for removable insertion in the interior of a boot, shoe or other enclosed space such as an athletic bag, closet and/or locker for drying and deodorizing.

2. Prior Art

It is well known that boots and shoes frequently become damp or moist due to perspiration of the wearer's foot or exposure to damp conditions often resulting in odorous conditions and eventually causing dry rot within the sole. As such, the removal of moisture from a shoe or boot greatly extends the life of the footwear by limiting dry rot. Further, the durability of specialized shoes and boots worn for activities such as ice skating, roller-blading, hiking, or other strenuous activities are often limited by damage caused by prolonged exposure to moisture. Various devices for drying and deodorizing footwear have been proposed, however existing devices have not been satisfactory or commercially successful, due primarily to their inability to effectively absorb moisture, their cost, and/or their difficulty of use.

Existing odor and moisture removing devices suitable for use in a shoe or boot have several disadvantages. Odor and moisture removers incorporated into plastic balls, pads, powders or other apparatus are ineffective at eliminating odor and moisture. Further, other existing devices either contribute to the weight of the shoe while worn or require application of sprays or powders, which are not reusable. Finally, the complexity of mechanical shoe dehumidifiers dramatically increases the cost of the unit and prevents the apparatus from being widely used.

Prior inventions that relate generally to shoe preservers include U.S. Pat. No. 5,291,669 to Khoury which discloses a pair of flexible, porous shoe drying inserts that include a material for absorbing moisture which are connected by a flexible strap for carrying the shoes together.

U.S. Pat. No. 3,131,036 to Hirschberg discloses a shoe-drying apparatus having porous semi-rigid plastic foam wherein the foam defines a cavity which is filled with a powdered desiccant material.

U.S. Pat. No. 896,536 to Hayden discloses a shoe tree having an absorbent sponge material surrounded by a porous fabric, wherein a wooden block or piece is disposed within the sponge material to provide for insertion and removal of the shoe tree.

U.S. Pat. No. 2,173,528 to Beale discloses a disinfectant pad including an absorbent material enclosed by a porous covering.

Other exemplary devices are shown in U.S. Pat. Nos. 5,980,913; 5,951,799; 5,950,323; 5,980,913; 5,921,003; 5,829,167; 5,826,349; 5,753,357; 5,733,826; 5,539,980; 5,732,485; 5,291,669; and 5,261,169.

SUMMARY OF THE INVENTION

The present invention comprises an apparatus of various designs that can be removably inserted into a shoe, boot, other footwear or other enclosed space such as an athletic bag, closet and/or locker to remove odor and moisture from the footwear. In the embodiment described herein, the invention comprises an outer shell with top and bottom pieces formed form a durable, wicking fabric such as polar fleece. The outer shell encloses an internal envelope composed of four layers of closely woven porous cloth. Between the first and second layer and the third and fourth layer of the woven porous cloth, there is placed a thick felted material infused with a pleasantly scented essential oil or fragrance. The first and fourth layer also provide a dust shield. Such a configuration effectively draws moisture from the footwear into the apparatus where the moisture is absorbed by a desiccant material.

Specifically, the apparatus functions by drawing moisture into the center of the apparatus by the wicking action of the layers of fabric and the desiccant material placed therein. Moisture from the inside of the shoe passes through the wicking material, past an envelope made from any porous woven material preferably, a porous woven material known generally in the industry as "muslin", is used herein. The moisture passes through the woven material and the thick felted material that retains essential oil or fragrance and into the desiccant material within the center of the apparatus. The ability of the desiccant material to absorb a large amount of moisture allows the apparatus to draw the moisture from the user's shoe or boot.

As an option, an essential oil or fragrance is infused in one or more sections of the apparatus to give the shoe a pleasant scent. Preferably, the essential oil or fragrance would be infused within a separate fabric element (preferably a fabric generally known as "silence cloth") enclosed with the woven porous material layers thereby separating the essential oil or fragrance from the absorbent desiccant material located within the center of the apparatus. The apparatus may also be manufactured without the infusion of essential oil or fragrance providing an essentially fragrance free product.

The completed, filled outer shell may have any dimensions necessary to removably fit within a shoe, boot, bag, closet, locker or the like. The dimensions may be easily adjusted in order to provide an apparatus of sufficient size to meet any demand.

Preferably, the pieces forming the external envelope are stitched together using a straight stitch. The internal envelope is stitched together using internal double over-locked stitching as known in the industry. Such a stitching method is well known in the industry. The color of the outer shell can be selected from any hue which suits the purchasing trends of the present consumer. Applicants also envision the inclusion of novelty design features, patterns or other non-functional elements on the external surface of the apparatus. The present invention in its broader, non-functional aspects comprises an imaginary creature that includes but is not limited to eyes and a tail. Expressing the functional aspects of the apparatus in a whimsical design of an animal or other 'creature' introduces an element of fun to the use of the invention. The polar fleece outer shell allows for the ease of manipulation when inserting or removing the apparatus into a shoe or boot. In addition to the functional configuration, both the element of fun and the ease of use differentiate the present invention from others in the past.

Therefore, it is the primary object of the invention to provide an apparatus for removing an odor and moisture which effectively reduces moisture and odor when placed within any confined area such as shoes or boots.

It is an additional object of the invention to provide a method of manufacturing an odor and moisture remover which effective reduces moisture and odor when placed within a confined area such as a shoe, boot, athletic bag, closet or locker.

It is an additional object of the invention to provide an apparatus for removing odor and moisture from confined areas which has a novel animal-like shape which appeals to the aesthetic sensibilities of the user.

It is an additional object of the invention to provide an apparatus for removing an odor and moisture from confined areas which can be easily inserted and removed from a shoe or boot.

It is yet another object of the invention to provide a functional apparatus for removing odor and moisture which is durable, and easily manufactured.

It is yet another object of the invention to provide a functional apparatus for removing an odor and moisture which can be used in a confined environment such as a shoe or boot and also an athletic bag, closet, and/or locker.

It is yet another object of the invention to provide an apparatus for removing odor and moisture with a sufficient amount of desiccant material to absorb any excess moisture which may exist in a substantially confined environment or area such as a shoe, boot, athletic bag, closet, and/or locker while simultaneously masking and neutralizing any odors which may exist in the immediate environment.

Various other features, objects and advantages of the present invention, other than those specifically set forth above, will become apparent in the following detailed description, drawings and claims.

DETAILED DESCRIPTION OF THE INVENTION

Figure 1:
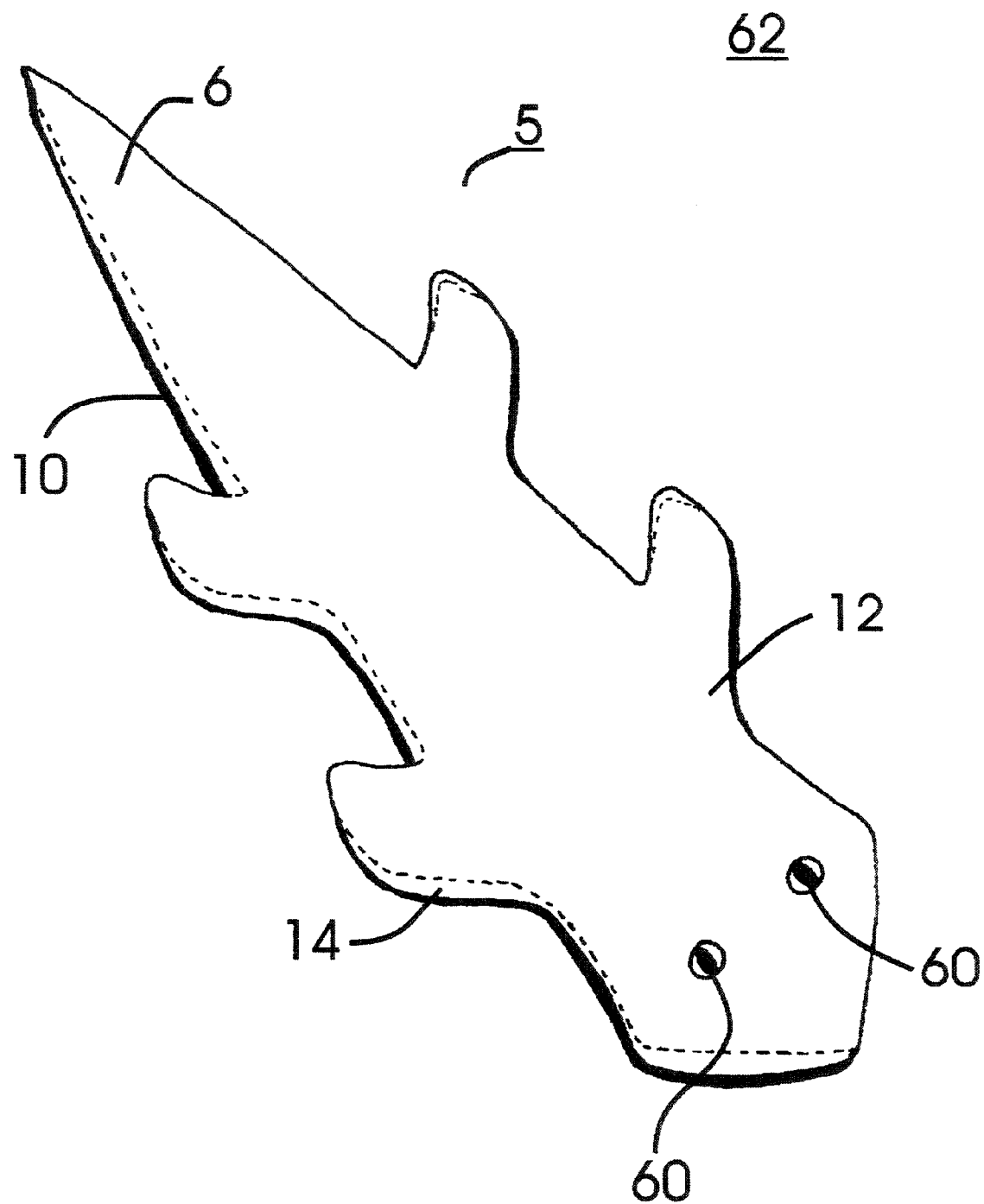
FIG. 1 is a perspective view of the odor and moisture removing apparatus.

FIG. 1 shows a perspective view of a basic version of the apparatus for removing odor and moisture from a confined area. The outer shell 10 is made from any suitable material with wicking properties. In a preferred embodiment, the outer shell 10 is manufactured from a fabric commonly known in the industry as polar fleece. When the apparatus 5 is placed inside a shoe 16 (as seen in FIGS. 2 and 3) or boot (not shown), the polar fleece 10 wicks the moisture 15 from the inside of the shoe 16 (as seen in FIGS. 2 and 3) or boot (not shown) into apparatus 5.

Figure 2:
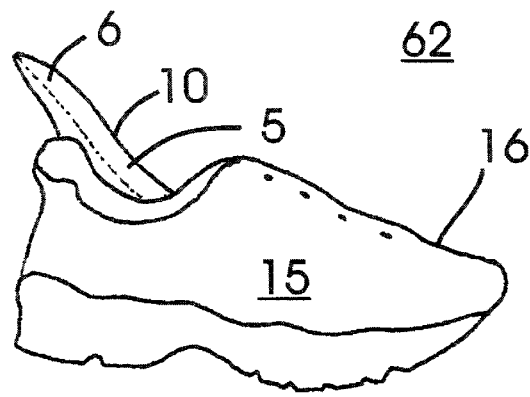
FIG. 2 is a side view of the apparatus of FIG. 1 being inserted in an athletic shoe.
Figure 3:
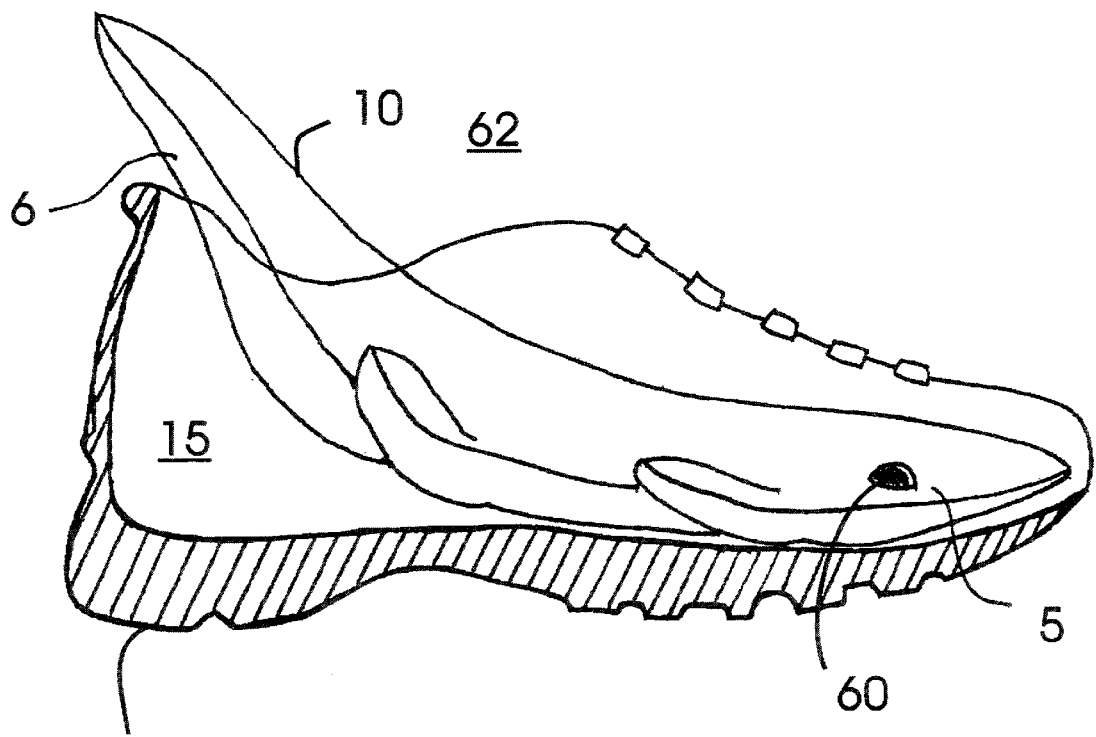
FIG. 3 is a cross section of the apparatus of FIGS. 1 and 2 shown within an athletic shoe.
Figure 4:
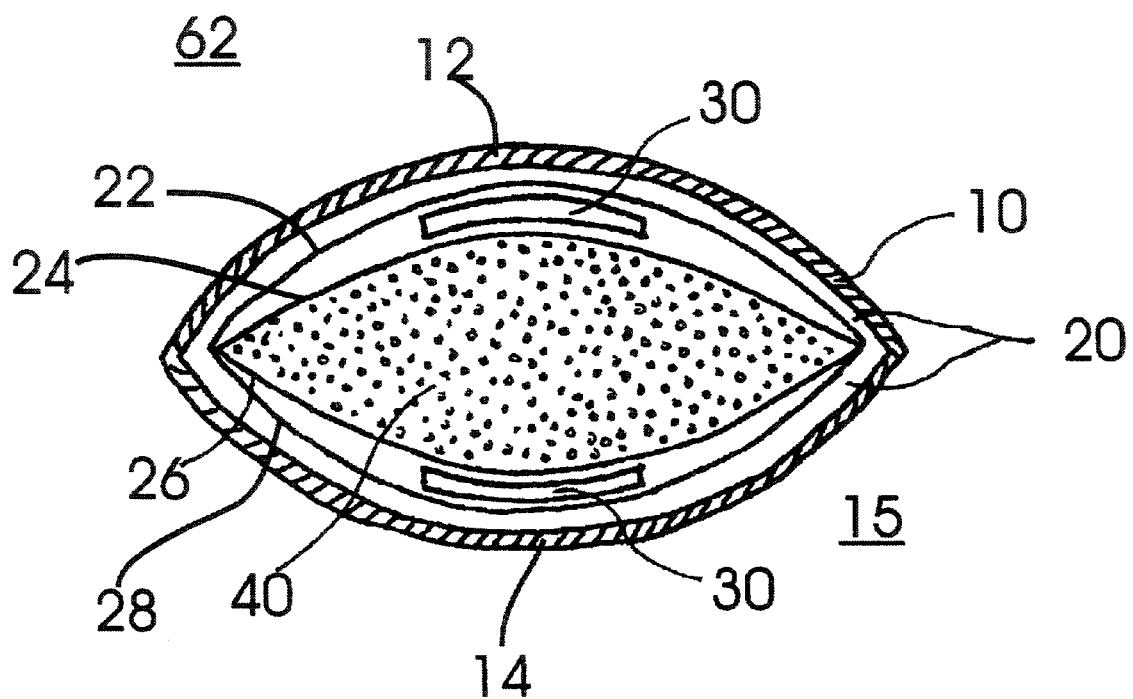
FIG. 4 is a cross section of the apparatus depicted in FIGS. 1 through 3.

As seen in FIGS. 2 and 3, the apparatus 7 is shown inside an athletic shoe 16. Placing the apparatus 5 inside of a shoe 16 allows the polar fleece outer shell 10 to draw moisture 15 to the absorbing desiccant material 40 (as best depicted in FIG. 4). While in use, moisture 15 absorbed by the apparatus 5 is released into the surrounding atmosphere 62 though the 'tail' portion 6 of the apparatus 5 which projects outside of the shoe 16 or boot. The tail or extension portion is substantially opposed from the eyes 60 of the apparatus, when it is embodied in a whimsical design. The extended portion allows for the facile removal of the apparatus from footwear or other substantially confined areas. It also is present to facilitate wicking of moisture from footwear or other substantially confined area. Removal of the apparatus 5 from the inside of a shoe 16, boot (not shown) or other enclosed space (not shown), also allows the moisture 15 from the desiccant material 40 to be released into the surrounding atmosphere 62.

Figure 5:
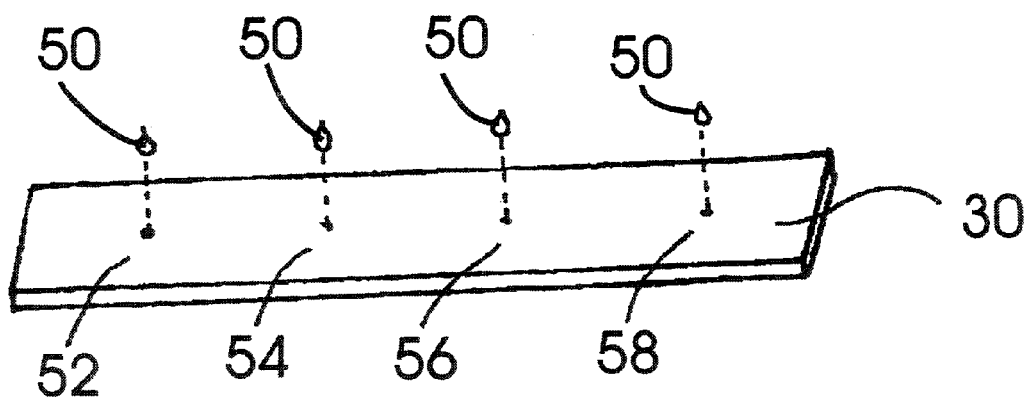
FIG. 5 is a plan view of the internal fabric element enclosed within the woven porous layers of the apparatus depicting points at which the essential oil or fragrance is placed.

As shown in FIG. 4, the apparatus 5 consists of an outer shell 10 with a top or first portion 12 and bottom or second portion 14 formed from a wicking fabric such as polar fleece. As shown, the outer shell 10 encapsulates a multi-layered closely woven fabric dust shield 20 which contains an absorbent, desiccant material 40. The dust shield 20 may be made from a closely woven cotton material or any other natural or synthetic material with wicking properties such as WickAWay® manufactured by Domestic Industries Inc. The dust shield 20 is sewn together as four layers 22, 24, 26, 28 generally in the form of an envelope. Between the first 22 and second 24 layers and between the third 26 and fourth 28 layers of the dust shield 20 are absorbent members 30 which may be any moisture or odor absorbing material, however, preferably, cotton felt members, such as a "silence cloth," available from Standard Textile Co. The absorbing desiccant material 40 is located between the second 24 and third layers 26 of the porous dust shield 20. As shown in FIG. 5, each absorbent porous felted fabric such as "silence cloth" member 30 is infused at several points with an essential oil 50 separate from the absorbing desiccant material 40 The points relate to receiving areas 52, 54, 56 and 58. The essential oil may be any oil suitable for the purpose of providing a pleasant fragrance to the apparatus and desiccant. Preferred oils are vanilla and cinnamon.

The desiccant material 40 may be any substance with moisture absorbing properties which can be safely included in a consumer product. One or more of the following materials, either alone or in combination may be utilized: calcium oxide; silica gel; sodium bicarbonate; bentonite; attapulgite; montmorillonite; ball clay; fire clay; Fuller's earth; carboxymethyl cellulose; polyionic cellulose; hydroxyethyl cellulose; pectin; carrageenan; or alginae. Additionally, the desiccant material 40 may be selected from any commercially available odor and moisture absorbing granular product used for the waste of household pets ('cat litter') or a combination of 'cat litter' and one or more of the materials listed above. Further, activated charcoal may be added to the desiccant material 40 to increase the effectiveness of the apparatus 5. As shown in the preferred embodiment, the desiccant material is a commercially available cat litter product.

Figure 6:
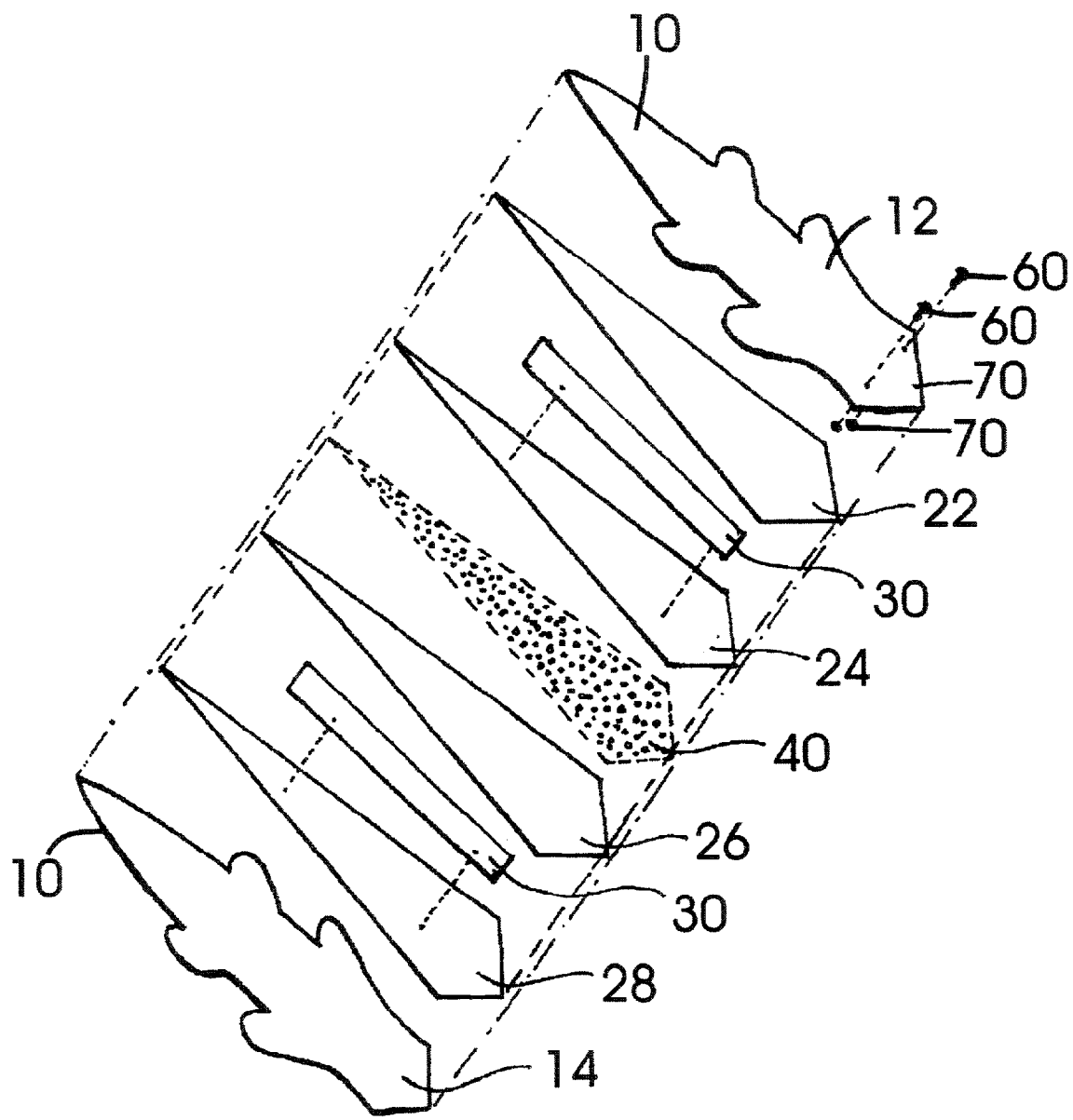
FIG. 6 is an exploded view of the apparatus depicted in FIGS. 1 through 5.
Figure 7:
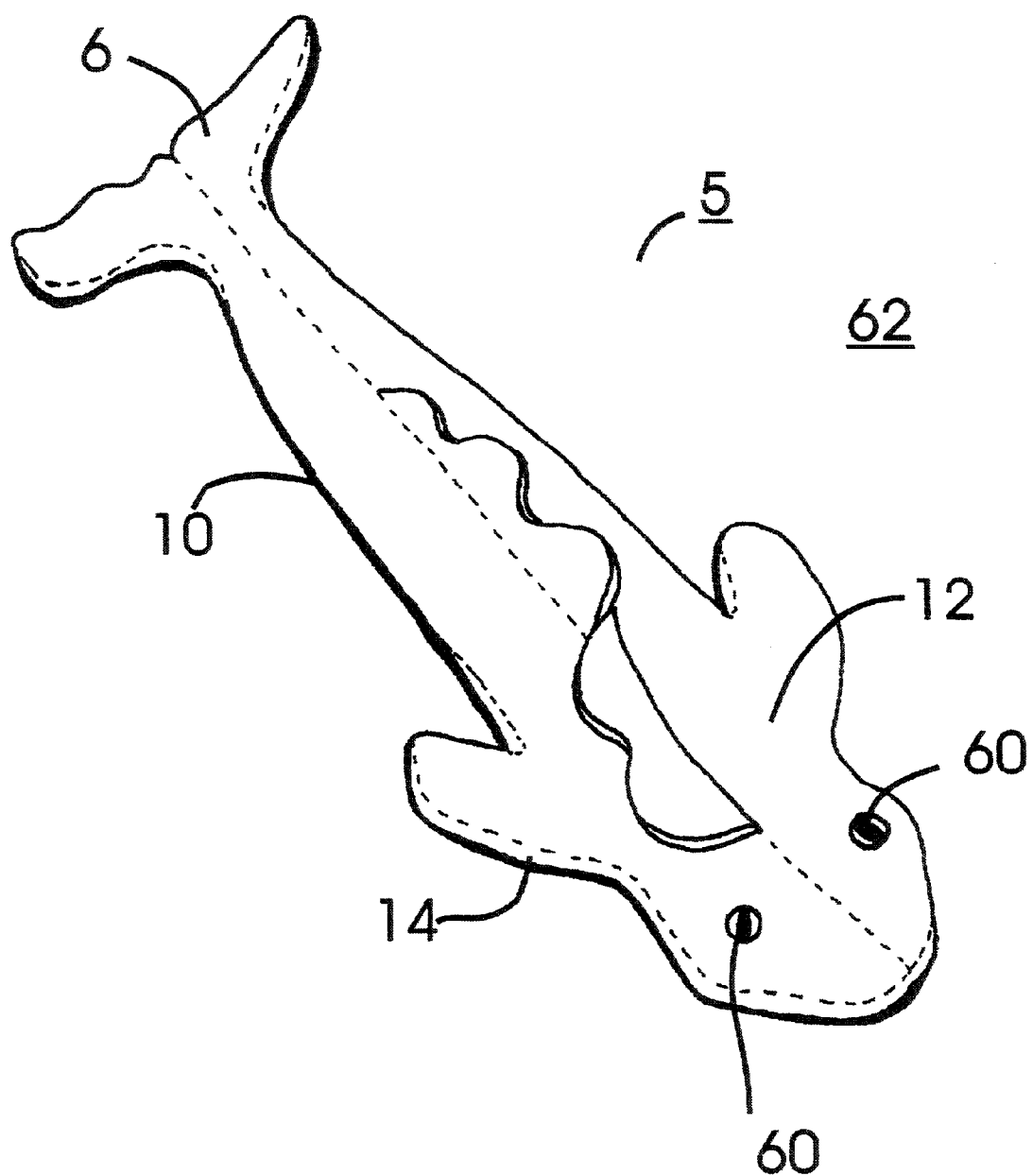
FIG. 7 is a perspective view of an alternative embodiment of the apparatus depicted in FIG. 1.
Figure 8:
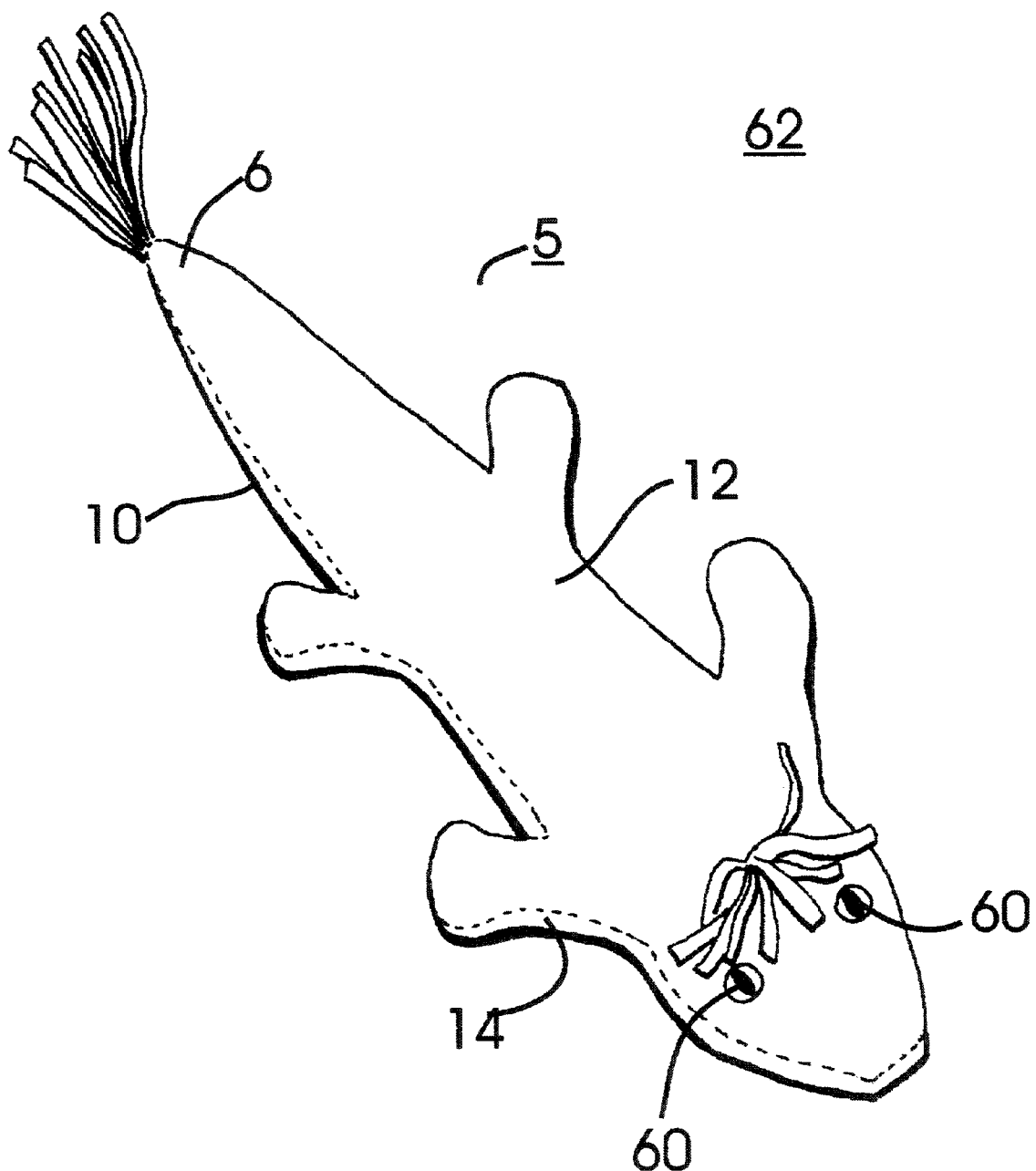
FIG. 8 is a perspective view of an additional alternative embodiment of the apparatus depicted in FIG. 1.

FIG. 6 shows an exploded view of the apparatus 5 including non-functional plastic eyes 60 and grommets 70 to affix the plastic eyes 60 to the outer shell 10. As shown in FIG. 6, the porous felted fabric members 30, essential oil 50, first 22, second 24, third 26 and fourth 28 layers of the dust shield 20 and the absorbing desiccant material 40 are assembled and inserted within the polar fleece outer shell 10 as a single unit.

In an alternative embodiment, the apparatus 5 may include a rigid member (not shown) extending across the length of the apparatus 5 to facilitate the placement of the apparatus 5 completely within the user's shoe 16 or boot (not shown). The shape or design of the apparatus may be animal like or any imaginary creature. The whimsical design may create a novel appearance when the non-functional elements are selected from the group consisting of anthropomorphic, zoomorphic, therianthropic and theriomorphic.

While a preferred embodiment of the invention has been shown and described with particularity, it will be appreciated that various changes and modifications may suggest themselves to one having ordinary skill in the art upon being apprised of the present invention. It is intended to encompass all such changes and modifications which fall within the scope and spirit of the appended claims. Various additional features and advantages of the invention are set forth in the following claims.

What is claimed is:

1. An apparatus for removing odor and moisture from an substantially confined area comprising:

an outer shell with a first portion and second portion;

a dust shield comprising first, second, third and fourth layers;

an absorbent member for carrying an aromatic material located between the first and second and third and fourth layers of the dust shield and;

an absorbing desiccant material located between the second and third layers of the dust shield.

2. The apparatus of claim 1 wherein said first and second portions of the outer shell are fabric which wicks moisture and odor.

3. The apparatus of claim 2 wherein wicking fabric of the outer shell is polar fleece.

4. The apparatus of claim 1 wherein the envelope is a closely woven material which wicks moisture and odors.

5. The apparatus of claim 1 wherein the absorbent member is a porous felted fabric.

6. The apparatus of claim 1 wherein said desiccant material is selected from the group consisting of calcium oxide; silica gel; sodium bicarbonate; bentonite; attapulgite; montmorillonite; ball clay; fire clay; Fuller's earth; carboxymethyl cellulose; polyionic cellulose; hydroxyethyl cellulose; pectin; carrageenan; alginae; and activated charcoal.

7. The apparatus of claim 6 wherein said desiccant material is cat litter.

8. The apparatus of claim 1 wherein an aromatic substance is applied to mask and eliminate odors.

9. The apparatus of claim 8 wherein the aromatic substance is an essential oil or fragrance.

10. The apparatus of claim 9 wherein said the essential oil is selected from the group consisting of cinnamon and vanilla.

11. The apparatus of claim 8 wherein non-functional elements are affixed thereto to provide a novelty appearance to the apparatus wherein the non-functional elements are selected from the group consisting of anthropomorphic, zoomorphic, therianthropic and theriomorphic.

12. The apparatus of claim 1 further comprising a tail or extended portion, that when positioned in footwear or other substantially confined area facilitates the removal of moisture thereof due to the positioning of the tail or extended portion outside of the footwear or confined area.

13. The apparatus of claim 12 wherein said extended portion or tail facilitates the removal of moisture from footwear or other substantially confined area by wicking action.

14. The apparatus of claim 12 wherein said extended portion or tail when placed in footwear or a substantially confined area where moisture is to be removed, serves to release moisture into the environment.

* * * * *